United States Patent
Borut

(10) Patent No.: US 11,627,953 B2
(45) Date of Patent: Apr. 18, 2023

(54) SURGICAL RETRACTOR HAVING A FLEXIBLE AIR-IMPERMEABLE BAG

(71) Applicant: Jeffrey J. Borut, Woodbury, MN (US)

(72) Inventor: Jeffrey J. Borut, Woodbury, MN (US)

(*) Notice: Subject to any disclaimer, the term of this patent is extended or adjusted under 35 U.S.C. 154(b) by 0 days.

(21) Appl. No.: 17/693,193

(22) Filed: Mar. 11, 2022

(65) Prior Publication Data
US 2022/0287701 A1 Sep. 15, 2022

Related U.S. Application Data

(60) Provisional application No. 63/159,876, filed on Mar. 11, 2021.

(51) Int. Cl.
*A61B 17/02* (2006.01)
*A61B 90/35* (2016.01)
*A61B 90/30* (2016.01)
*A61B 17/00* (2006.01)

(52) U.S. Cl.
CPC ...... *A61B 17/0218* (2013.01); *A61B 17/0206* (2013.01); *A61B 90/35* (2016.02); *A61B 2017/00557* (2013.01); *A61B 2090/306* (2016.02)

(58) Field of Classification Search
CPC ................ A61B 17/0206; A61B 90/35; A61B 2017/0057

USPC ................................................. 600/201–245
See application file for complete search history.

(56) References Cited

U.S. PATENT DOCUMENTS 5,159,921 A * 11/1992 Hoover .............. A61B 17/0293
600/245
2011/0301420 A1* 12/2011 Pryor ..................... A61B 17/02
600/207

* cited by examiner

*Primary Examiner* — Eduardo C Robert
*Assistant Examiner* — Tara Rose E Carter
(74) *Attorney, Agent, or Firm* — Haynes and Boone, LLP

(57) ABSTRACT

A surgical retractor for positioning within an incision within a body of a patient is described. The surgical retractor comprises a flexible air-impermeable bag surrounding an interior region and extending from a first end through a central region to a second end. The surgical retractor includes a first port in the central region, the flexible air-impermeable bag surrounding a first channel that extends from the first port towards the first end, a second port in the central region, the flexible air-impermeable bag surrounding a second channel that extends from the second port toward the second end, and a plurality of beads substantially filling the interior region of the flexible air-impermeable bag. The flexible air-impermeable bag is configured to rigidify in response to air being evacuated from the interior region to position and hold intra-incision contents within a surgical working space in a patient.

20 Claims, 11 Drawing Sheets

SURGICAL RETRACTOR HAVING A FLEXIBLE AIR-IMPERMEABLE BAG

CROSS-REFERENCE TO RELATED APPLICATIONS

This application claims priority to and the benefit of U.S. Provisional Patent Application No. 63/159,876 filed Mar. 11, 2021 and entitled "SURGICAL RETRACTOR HAVING A FLEXIBLE AIR-IMPERMEABLE BAG," which is hereby incorporated by reference in its entirety.

TECHNICAL FIELD

The present disclosure is related to surgical instruments, and in particular, to surgical retractors.

BACKGROUND

Medical retractors are surgical instruments used during surgery and other clinical procedures to separate the edges of a surgical incision or wound, or to hold back underlying organs and tissues so that body parts exposed by the incision may be accessed by a surgeon or clinician. Medical retractors are commonly handheld metal tools possessing a curved, hooked, or angled blade that are held in place by a supporting framework. With the retractors properly positioned on the supporting framework, the surgical field is cleared. For example, medical retractors are typically placed at opposite sides of the incision to expand the incision for surgery.

Unfortunately, a problem with existing medical retractors is that it can be cumbersome and time-consuming to setup the supporting framework and also to fasten the retractors to the supporting framework in the proper position. The assembly of the supporting framework and attachment of the retractors may thus involve substantial delay. The resulting delay may worsen patient outcomes, particularly in the case of trauma. As such, there is a need for a system and method that addresses this problem.

SUMMARY

In accordance with a first aspect of the disclosure, a surgical retractor is provided that includes: a flexible air-impermeable bag surrounding an interior region and extending from a first end through a central region to a second end; a first port in the central region, the flexible air-impermeable bag surrounding a first channel that extends from the first port towards the first end; a second port in the central region, the flexible air-impermeable bag surrounding a second channel that extends from the second port toward the second end; and a plurality of beads within the interior region of the flexible air-impermeable bag, wherein the flexible air-impermeable bag is configured to rigidify about the plurality of beads in response to air being evacuated from the interior region to position intra-incision contents within a surgical working space in a patient.

In accordance with a second aspect of the disclosure, a surgical retractor is provided that includes: a frame having a support structure, a first extending arm and a second extending arm, and a locking mechanism configured to lock the first extending arm and the second extending arm into a locked position; a flexible air-impermeable bag surrounding an interior region and extending from a first end through a central region to a second end; a first port in the central region, the flexible air-impermeable bag surrounding a first channel that extends from the first port towards the first end; a second port in the central region, the flexible air-impermeable bag surrounding a second channel that extends from the second port toward the second end; and a plurality of beads within the interior region of the flexible air-impermeable bag, wherein the first channel is configured to receive the first extending arm, the second channel is configured to receive the second extending arm, and the flexible air-impermeable bag is configured to rigidify about the plurality of beads in response to air being evacuated from the interior region to position and hold intra-incision contents within the surgical working space within the body of the patient.

In an example of operation, the flexible air-impermeable bag is fitted on the frame of the surgical retractor. The combination of the flexible air-impermeable bag and frame are inserted into the incision within the body of the patient. The air is then evacuated from the flexible air-impermeable bag to rigidify the air-impermeable bag within the surgical working space.

Other devices, apparatuses, systems, methods, features, and advantages of the invention will be or will become apparent to one with skill in the art upon examination of the following figures and detailed description. It is intended that all such additional devices, apparatuses, systems, methods, features, and advantages be included within this description, be within the scope of the invention, and be protected by the accompanying claims.

BRIEF DESCRIPTION OF THE FIGURES

The invention may be better understood by referring to the following figures. The components in the figures are not necessarily to scale, emphasis instead being placed upon illustrating the principles of the invention. In the figures, like reference numerals designate corresponding parts throughout the different views.

FIG. 9 is a perspective view of the surgical retractor, shown in FIG. 6, inserted into the incision of the torso area in accordance with the present disclosure.

FIG. 10 is a flowchart of a method performed by the surgical retractor shown in FIGS. 3A-7 in accordance with the present disclosure.

DETAILED DESCRIPTION

Figure 1A:
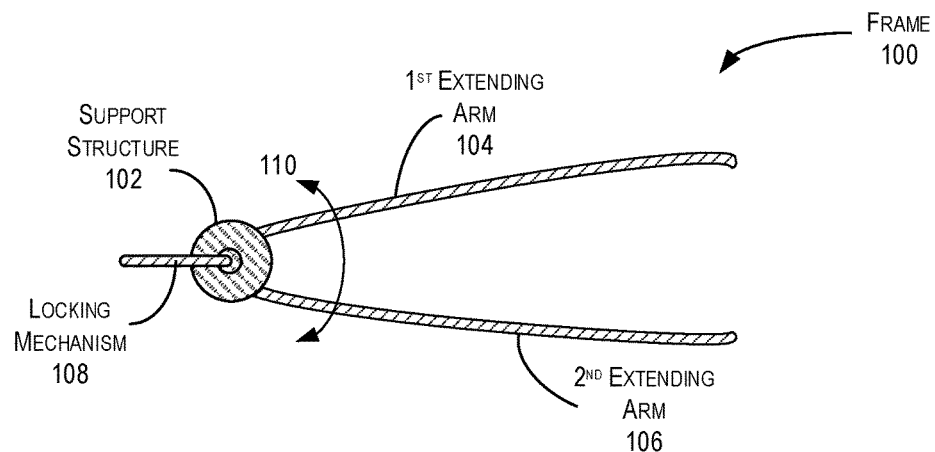
FIG. 1A is a top view of an example of an implementation of a frame of a surgical retractor in accordance with the present disclosure.

To provide an improved surgical retractor with significantly reduced setup time, a "beanbag" surgical retractor is provided. The use of beanbag positioners to position a patient for surgery or other medical procedures is well known. Such positioners include a flexible container or bag of small beads particles (the beans). Prior to use, the bag also contains air so the positioner functions like a conventional beanbag chair in that the beads are free to move within the bag. In this state, the patient may be comfortably positioned on the relaxed beanbag positioner. With the patient properly situated, air is then pumped out of the bag. The beads then become rigidly held within the evacuated bag due to atmospheric pressure. These flexible and rigid properties of a beanbag positioner are cleverly exploited herein so that a beanbag may function as a surgical retractor. In that regard, the disclosed beanbag surgical retractor may be positioned within a surgical incision in the body of a patient in the relaxed (non-evacuated) state. The clinician may thus position the relaxed beanbag surgical retractor so that the desired body portions (e.g., intestines or other internal organs) are or will be excluded from the operating field. With the relaxed beanbag surgical retractor in position, the clinician may then evacuate the air from the beanbag so that the beanbag surgical retractor becomes rigid.

Consider the advantages of such a beanbag surgical retractor—unlike conventional surgical retractors that require a laborious and time-consuming framework construction and setup, a beanbag surgical retractor may be quickly placed in the operating field and evacuated so that surgery may proceed. The surgery may then be performed more quickly, which improves patient outcomes. Indeed, the time savings provided by the expedited setup provided by a beanbag surgical retractor may be the difference between life and death in the case of trauma surgery.

Some example embodiments of a beanbag surgical retractor will now be discussed in more detail. For brevity, a beanbag surgical retractor will be denoted simply as a "surgical retractor" in the following discussion. The surgical retractor comprises a flexible air-impermeable bag surrounding an interior region and extending from a first end through a central region to a second end. The surgical retractor may include a first port in the central region, the flexible air-impermeable bag surrounding a first channel that extends from the first port towards the first end, a second port in the central region, the flexible air-impermeable bag surrounding a second channel that extends from the second port toward the second end, and a plurality of beads substantially filling the interior region of the flexible air-impermeable bag. The flexible air-impermeable bag is configured to rigidify in response to air being evacuated from the interior region to position and abut against undesired intra-incision contents within a surgical field in a patient. The surgical retractor may further include a frame having a first extending arm and a second extending arm extending outward from the frame. The first extending arm extends through the first port and the first channel to the first end and the second extending arm extends through the second port and the second channel to the second end.

In an example of operation, the flexible air-impermeable bag is fitted on the frame of the surgical retractor. The combination of the flexible air-impermeable bag and frame are inserted into the incision within the body of the patient and first extending arm and the second extending arm are retracted into the locked position. The air is then evacuated from the flexible air-impermeable bag to rigidify the air-impermeable bag within the surgical working space.

Figure 1B:
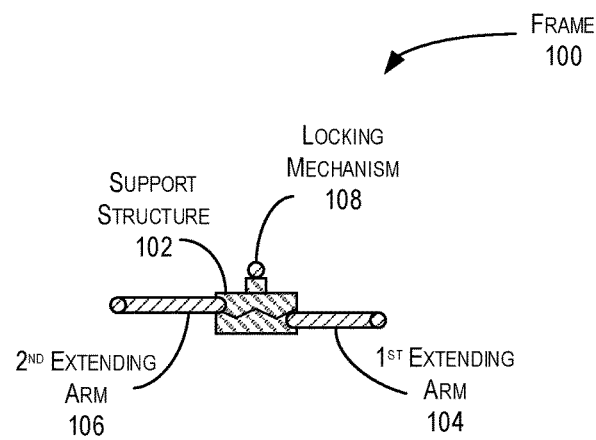
FIG. 1B is a front view of the frame shown in FIG. 1A in accordance with the present disclosure.
Figure 1C:
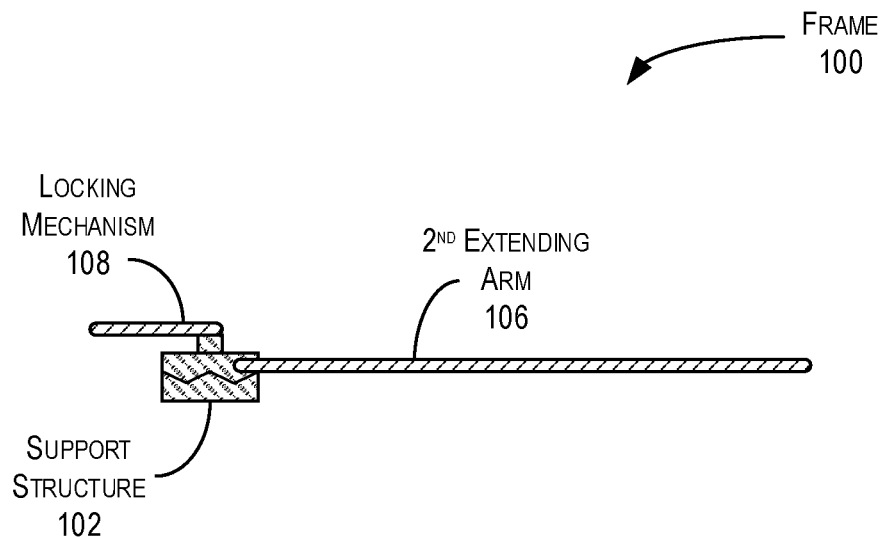
FIG. 1C is a first side view of the frame shown in FIGS. 1A and 1B in accordance with the present disclosure.
Figure 1D:
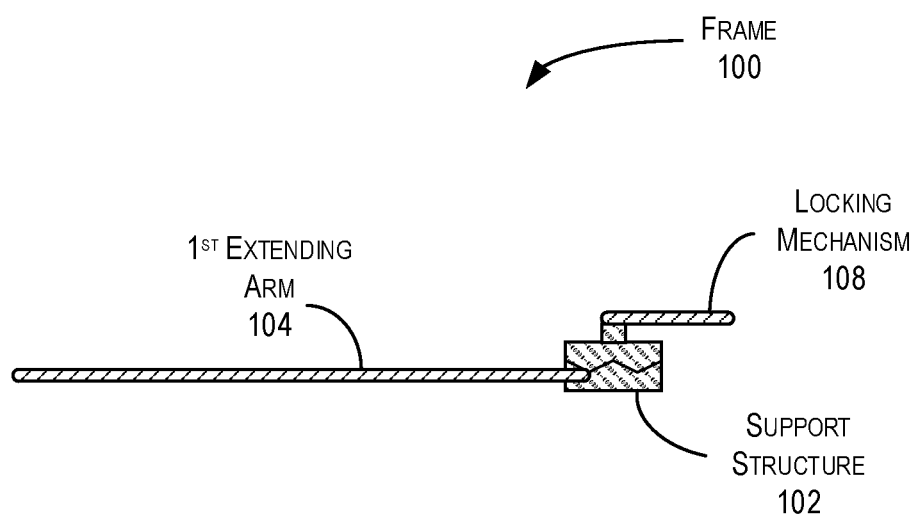
FIG. 1D is a second side view of the frame shown in FIGS. 1A through 1C in accordance with the present disclosure.

Turning now to the drawings, a top view of an example of an implementation of a frame 100 for use in surgical retractor is shown in FIG. 1A in accordance with the present disclosure. FIG. 1B is a front view, FIG. 1C is a side view, and FIG. 1D is a second side view of the frame 100 shown in FIG. 1A in accordance with the present disclosure.

In this example, the frame 100 includes a support structure 102, a first extending arm 104, a second extending arm 106, and a locking mechanism 108. The first extending arm 104 and second extending arm 106 extend from the support structure 102 and are configured to spread apart to hold the surgical retractor in substantially a "V-shaped" configuration to form a surgical working space for a surgeon within the patient. As an example, both the first extending arm 104 and second extending arm 106 may be straight or curved rods or bars that may be constructed of a strong rigid material such as, for example, metal, plastic, or ceramic. The support structure 102 may be any mechanical part, component, or device that is configured to hold the ends of the first extending arm 104 and second extending arm 106 to allow the first extending arm 104 and second extending arm 106 to be appropriately positioned within an arc 110. For example, the first extending arm 104 and second extending arm 106 may be straight or curved rods that extend outward from the support structure 102 within a desired position in arc 110.

In this example, the structural support 102 may also be constructed of a strong rigid material such as, for example, metal, plastic, or ceramic. The support structure 102 may include a mechanical locking mechanism 108 that is configured to lock the first extending arm 104 and second extending arm 106 within the desired positions in arc 110.

Figure 2A:
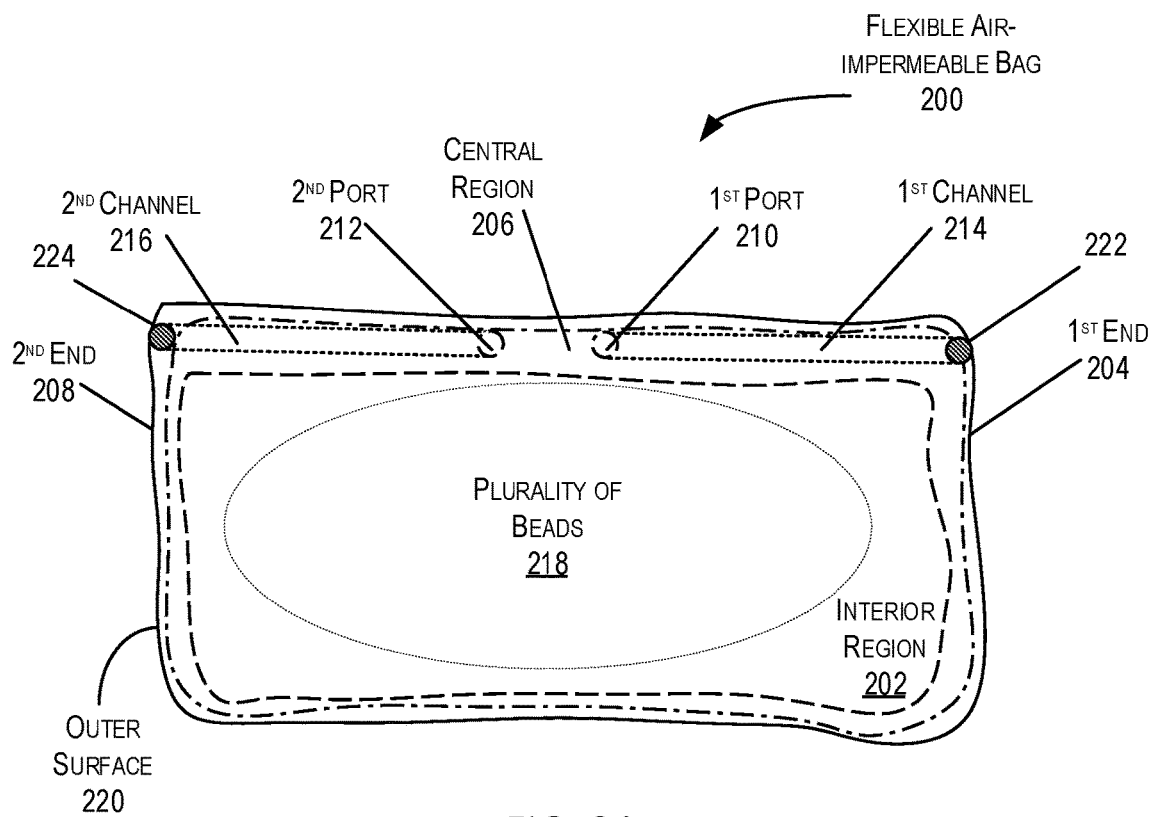
FIG. 2A is a front view of an example of an implementation of a flexible air-impermeable bag of a surgical retractor in accordance with the present disclosure.
Figure 2B:
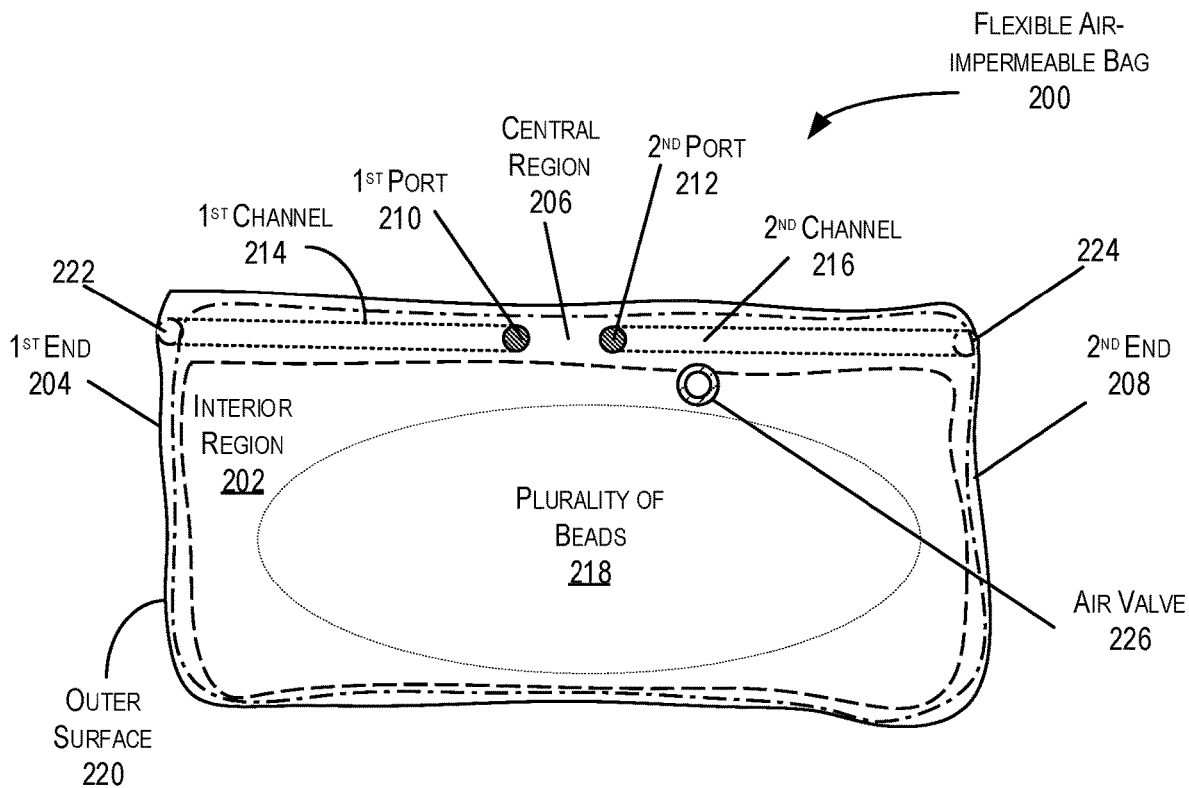
FIG. 2B is a back view of the flexible air-impermeable bag shown in FIG. 2A in accordance with the present disclosure.
Figure 2C:
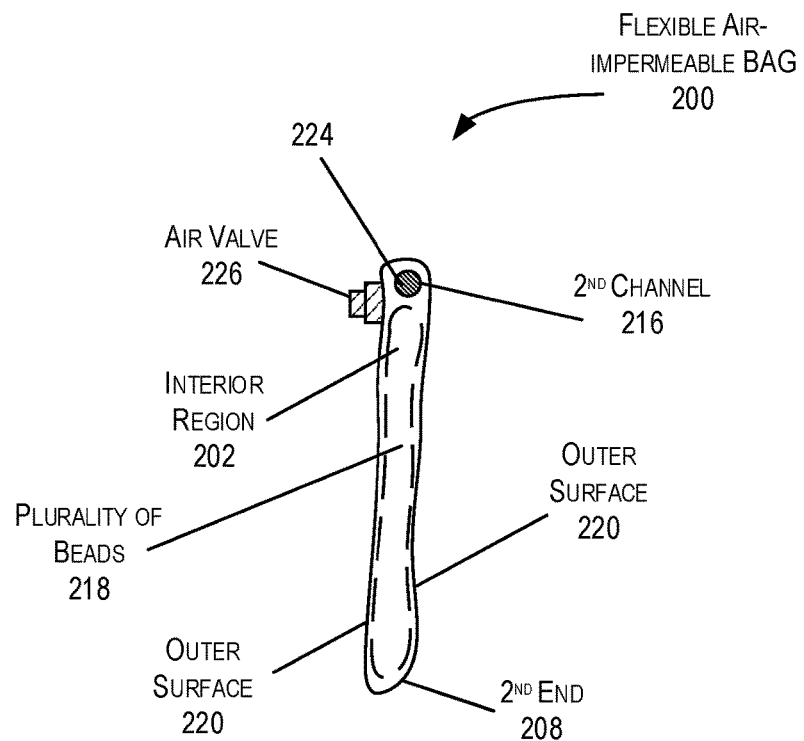
FIG. 2C is a side view of the flexible air-impermeable bag shown in FIGS. 2A and 2B in accordance with the present disclosure.
Figure 2D:
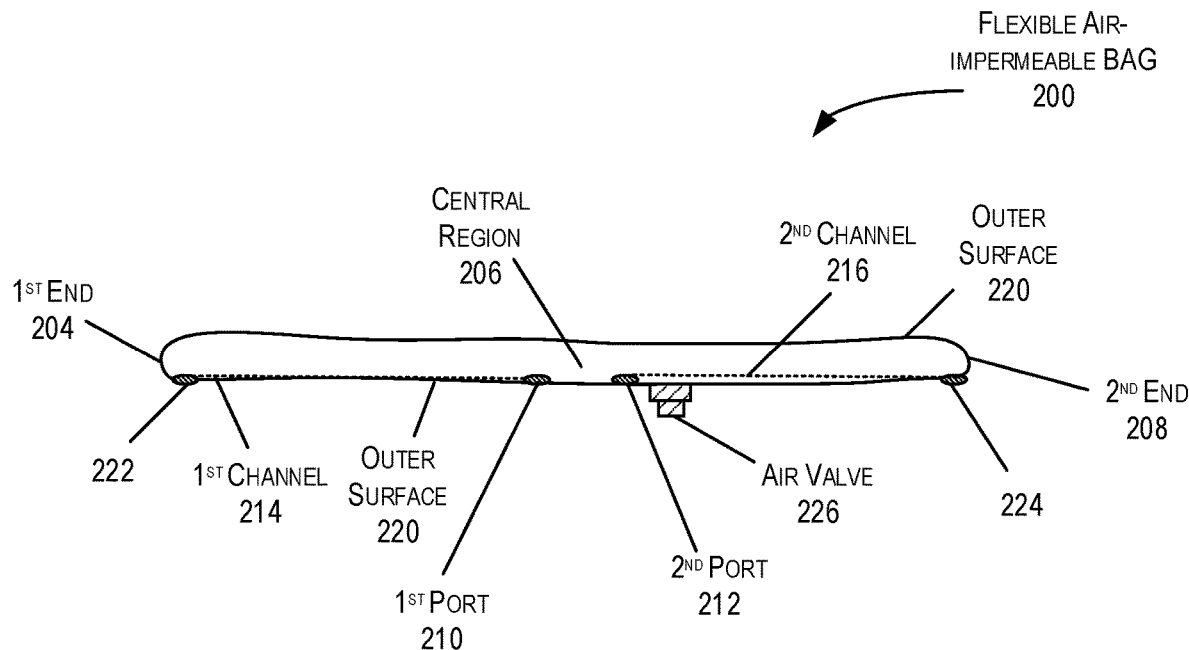
FIG. 2D is a top view of the flexible air-impermeable bag shown in FIGS. 2A through 2C in accordance with the present disclosure.

Turning now to FIGS. 2A through 2D, in FIG. 2A, a front view of an example flexible air-impermeable bag 200 is shown in accordance with the present disclosure. FIG. 2B is a back view, FIG. 2C is a side view, and FIG. 2D is a top view of the flexible air-impermeable bag 200 shown in FIG. 2A in accordance with the present disclosure.

The flexible air-impermeable bag 200 includes and surrounds an interior region 202 and extends from a first end 204 through a central region 206 to a second end 208. The flexible air-impermeable bag 200 also includes a first port 210 and second port 212 in the central region 206 and a first channel 214 and a second channel 216. The first channel 214 extends from the first port 210 to the first end 204 and the second channel 216 extends from the second port 212 to the second end 208. The flexible air-impermeable bag surrounds both the first channel 214 and the second channel 216 so as to exclude channels 214 and 216 from interior region 202. The flexible air-impermeable bag 200 further includes a plurality of beads 218 within the interior region 202 of the flexible air-impermeable bag 200. As noted earlier, beads 218 are loose within bag 200 prior to the evacuation of air from bag 200. But when air is evacuated from bag 200, bag 200 and beads 200 become rigid due to surrounding atmospheric pressure.

In this example, the flexible air-impermeable bag 200 includes an outer surface 220 that covers the first end 204, central region 206, and second end 208 of the flexible air-impermeable bag 200. The first port 210 and second port 212 have openings in the outer surface 220 on the backside of the flexible air-impermeable bag 200 at a first end of the first channel 214 and a first end of the second channel 216. The first channel 214 and the second channel 216 may include openings 222 and 224 at the first end 204 and second end 208, respectively, of the flexible air-impermeable bag 200. In other embodiments, first channel 214 and second channel 216 may be closed-ended such that opening 222 and 224 are absent.

During the evacuation, air is pumped from the flexible air-impermeable bag 200 through an air valve 226 that is connected to the interior region 202. The air valve 226 is optionally located on a back surface of the outer surface 220 of the flexible air-impermeable bag 200 and is configured to allow for the flow of air into and out of the interior region 202 of the flexible air-impermeable bag 200. The air valve 226 may include an airtight locking mechanism that allows for the air valve 226 to be shut or open.

In this example, the first port 210, first channel 214, and opening 222 is configured to allow the insertion of the first extending arm 104 and the second port 212, the second channel 216, and opening 224 is configured to allow the insertion of the second extending arm 106. As such, a top portion of the flexible air-impermeable bag 200 is configured to be mounted on the first extending arm 104 and on the second extending arm 106. The first extending arm 104 may optionally extend completely through the first channel 214 and out of the opening 222. Similarly, the second arm 106 may optionally extend completely through the second channel 216 and out of the opening 224.

The flexible air-impermeable bag 200 may be constructed of plastic, rubber, canvas, or other air-impermeable materials. In this example, the plurality of beads 218 substantially fill the interior region 202 of the flexible air-impermeable bag 200. The plurality of beads 218 in the interior region 202 may include beads constructed of metal, plastic, ceramic, or other type of rigid material. The number of beads in the plurality of beads 218 is determined by the design of the flexible air-impermeable bag 200 so as to allow the flexible air-impermeable bag 200 to have an outer surface 220 that is pliable prior to the evacuation of air from the internal region 202 and then rigid in response to the air being evacuated from the interior region 202 via the air valve 226.

Figure 3A:
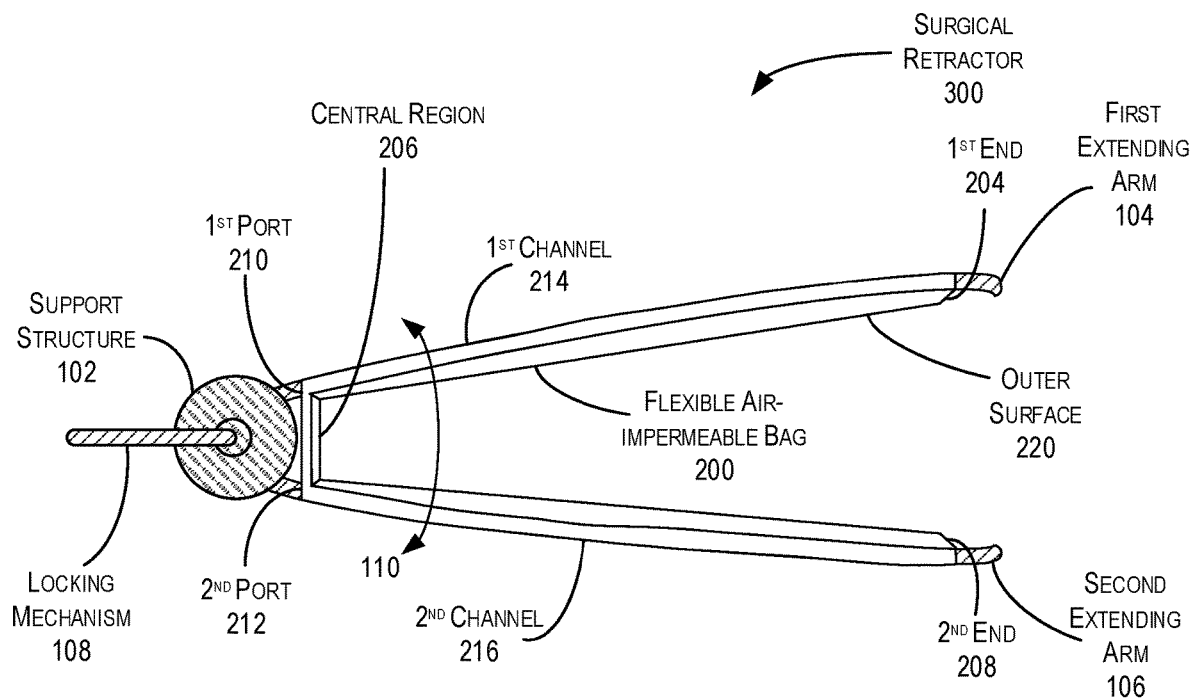
FIG. 3A is a top view of an example of an implementation of the surgical retractor having the frame and flexible air-impermeable bag shown in FIGS. 1A-2D in accordance with the present disclosure.
Figure 3B:
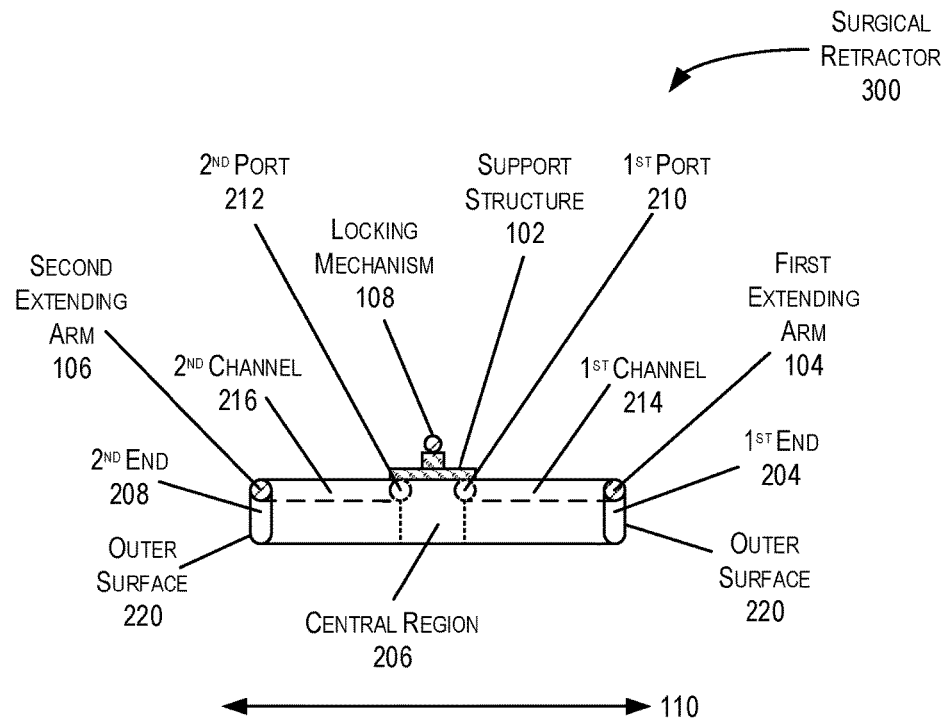
FIG. 3B is a front view of the surgical retractor shown in FIG. 3A in accordance with the present disclosure.
Figure 3C:
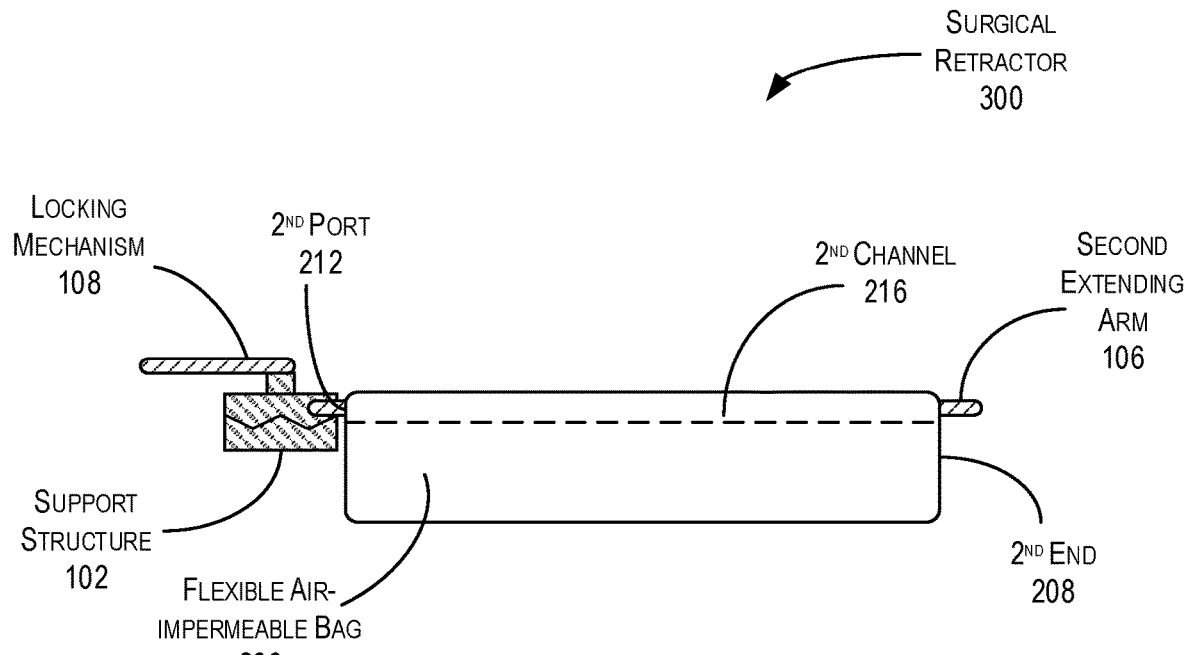
FIG. 3C is a first side view of the surgical retractor shown in FIGS. 3A and 3B in accordance with the present disclosure.
Figure 3D:
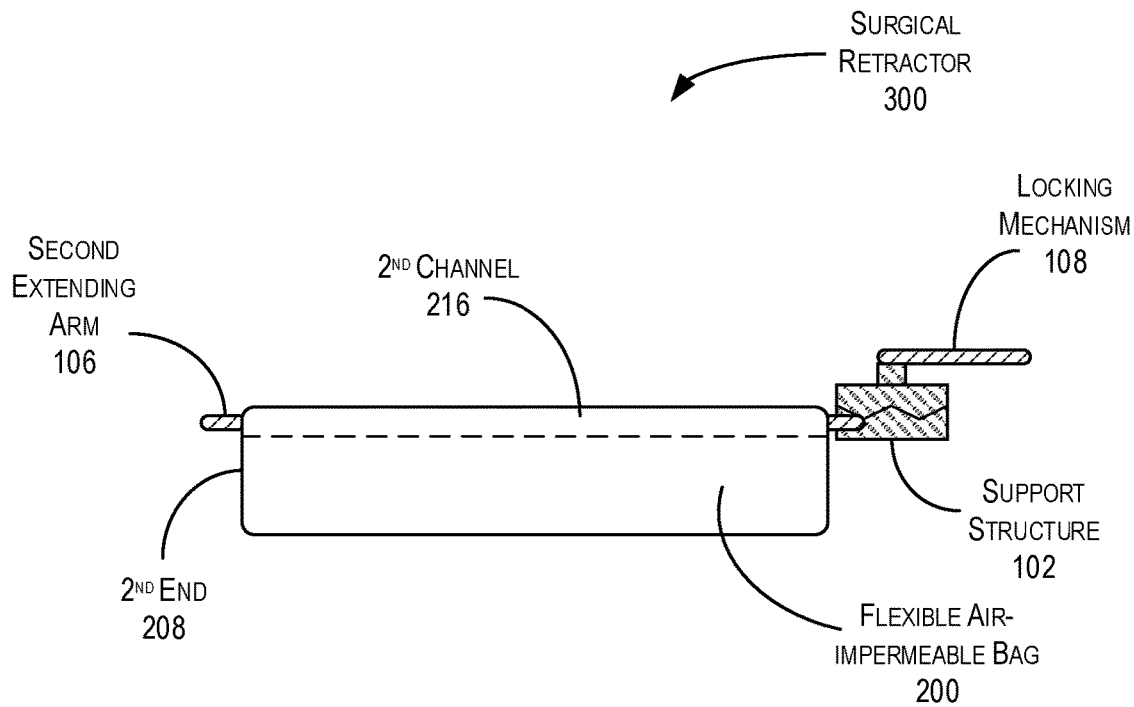
FIG. 3D is a second side view of the surgical retractor shown in FIGS. 3A through 3D in accordance with the present disclosure.

Turning to FIGS. 3A through 3D, an example surgical retractor 300 is shown in accordance with the present disclosure that includes frame 100 and bag 200. FIG. 3B is a front view, FIG. 3C is a first side view, and FIG. 3D is a second side view of the surgical retractor 300 shown in FIG. 3A in accordance with the present disclosure. In this example, the first extending arm 104 and second extending arm 106 are fitted into the first port 210 and the second port 210 of the flexible air-impermeable bag and passed through the first channel 214 and the second channel 216 to the first end 204 and second end 208, respectively. In this example, the first extending arm 104 and second extending arm 106 are shown as extending beyond the first end 204 and second end 206 of the flexible air-impermeable bag 200, however, it is appreciated by those of ordinary skill in the art that both first extending arm 104 and second extending arm 106 may be shorter and either extend to first end 204 and second end 208 or be shorter in alternative embodiments.

Figure 4:
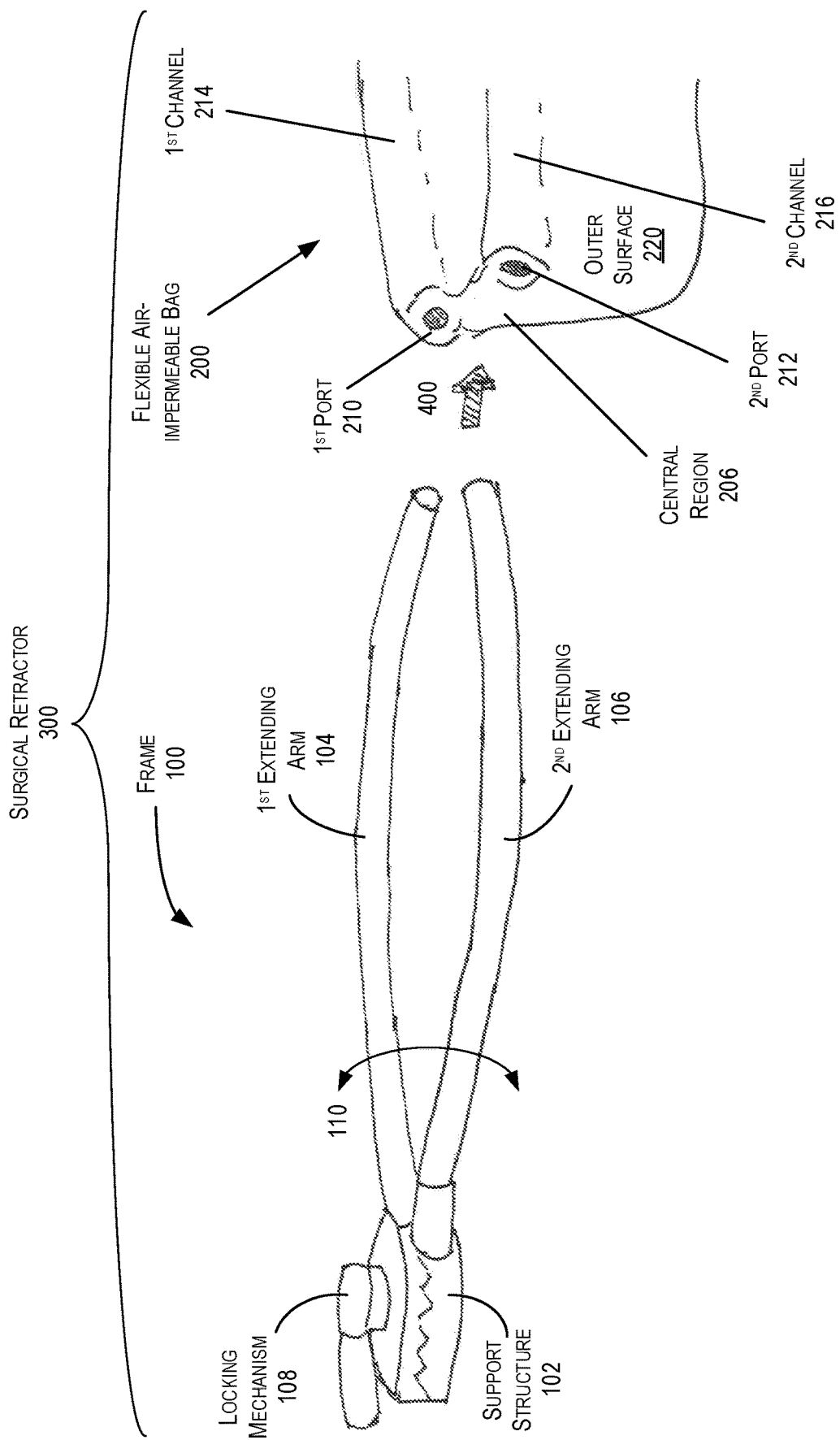
FIG. 4 is an assembly view of the frame and the flexible air-impermeable bag shown in FIGS. 3A through 3D.

In FIG. 4, an assembly view of the surgical retractor 300 is shown having the frame 100 and flexible air-impermeable bag 200 in accordance with the present disclosure. In this example, the flexible air-impermeable bag 200 is shown bent into an approximately V-shaped configuration and the first extending arm 104 and second extending arm 106 are inserted as shown by arrow 400 into the first channel 214 and second channel 216 at the central region 206 via the first port 210 and second port 212, respectively.

Figure 5:
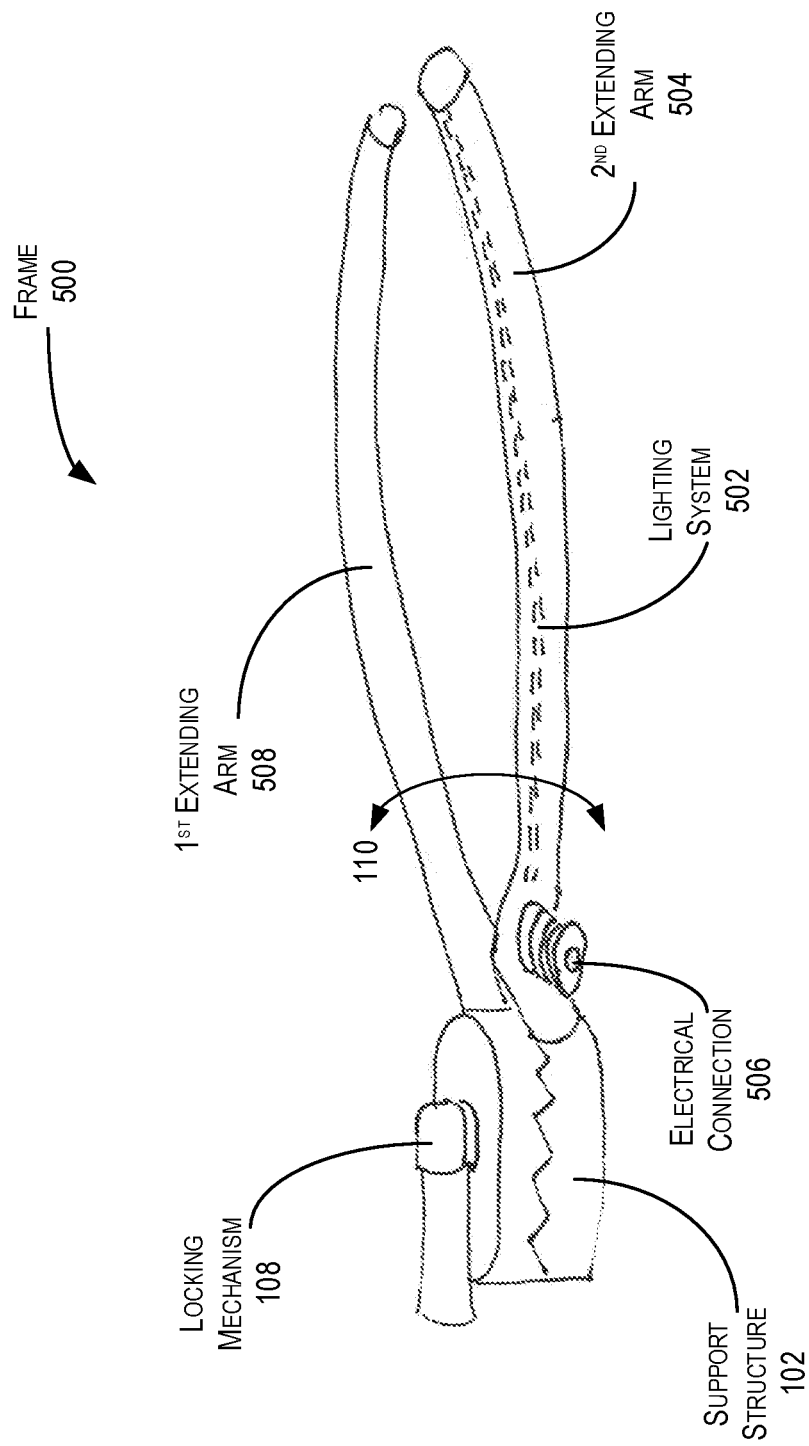
FIG. 5 is an assembly view of an example of another implementation of the frame in accordance with the present disclosure.

FIG. 5 is an assembly view of an example frame 500 in accordance with the present disclosure. The frame 500 includes a support structure 502 that includes a top portion 504 and a bottom portion 506 of the frame 500. In this example, the top portion 504 includes the attached first extending arm 508 and the bottom portion 506 includes the attached second extending arm 510. The top portion 504 of the support structure 502 also includes a locking mechanism 512. In this example, both the top portion 504 and bottom portion 506 of the support structure 502 may include, for example, corrugated surfaces 514 that are configured to moveably slide and lock in place relative to each other so as lock arms 510 and 508 in a desired position such as to support the V-shaped configuration of bag 200.

Figure 6:
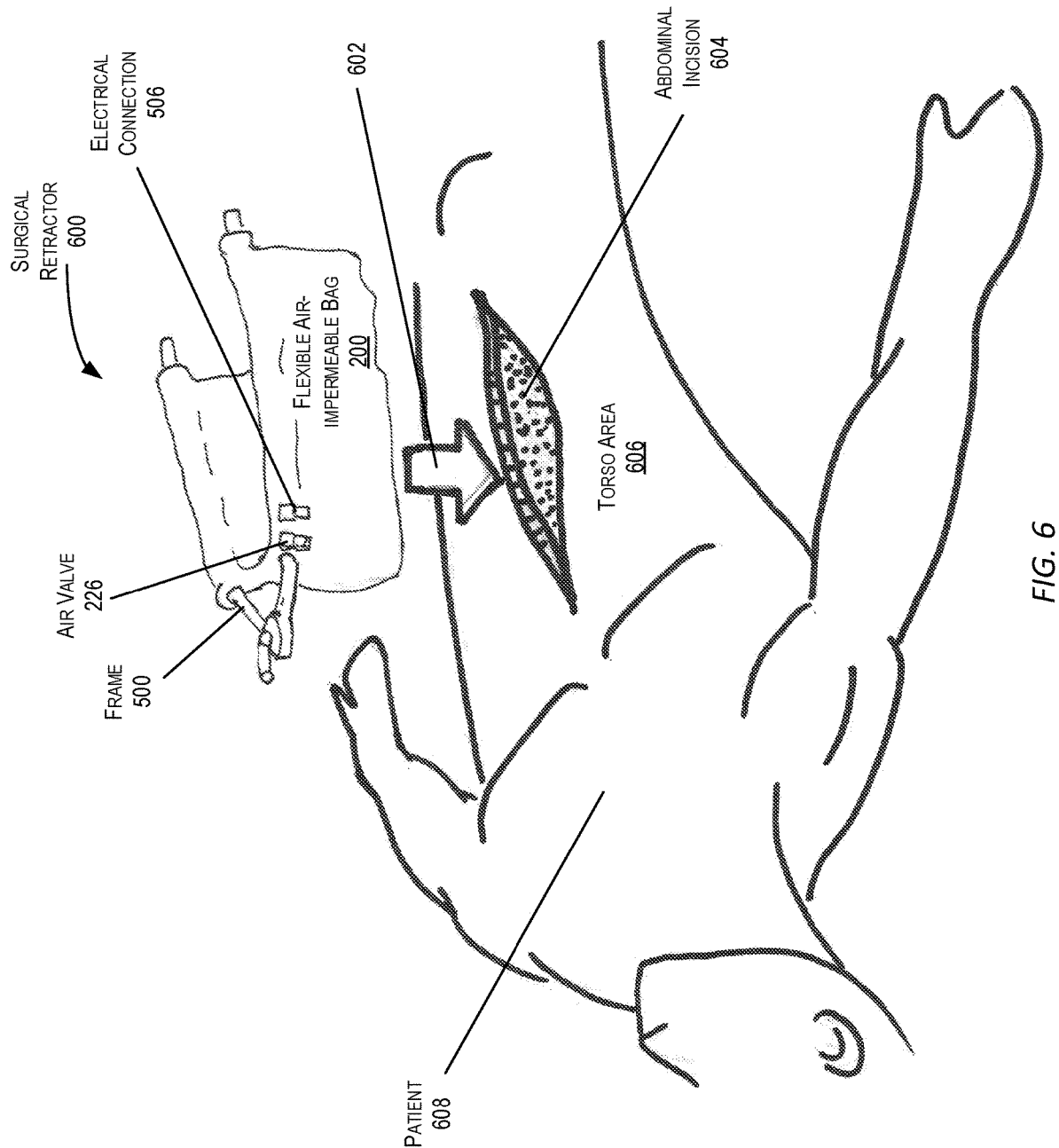
FIG. 6 is perspective view of an example of another implementation of the flexible air-impermeable bag in accordance with the present disclosure.

In FIG. 6, a perspective view of an example flexible air-impermeable bag 600 is shown in accordance with the present disclosure. In this example, the flexible air-impermeable bag 600 is shown in a relaxed (air not being evacuated) state without the frame 500 inserted through the first port (not shown) and second port 602. The flexible air-impermeable bag 600 includes an outer surface 604, a central region 606, a first channel 608, a second channel 610, a first end 612 and a second end 614. In this example, channels 608 and 610 are sealed at ends 612 and 614, respectively. In alternative implementations, channels 608 and 610 may be open at both ends.

Figure 7:
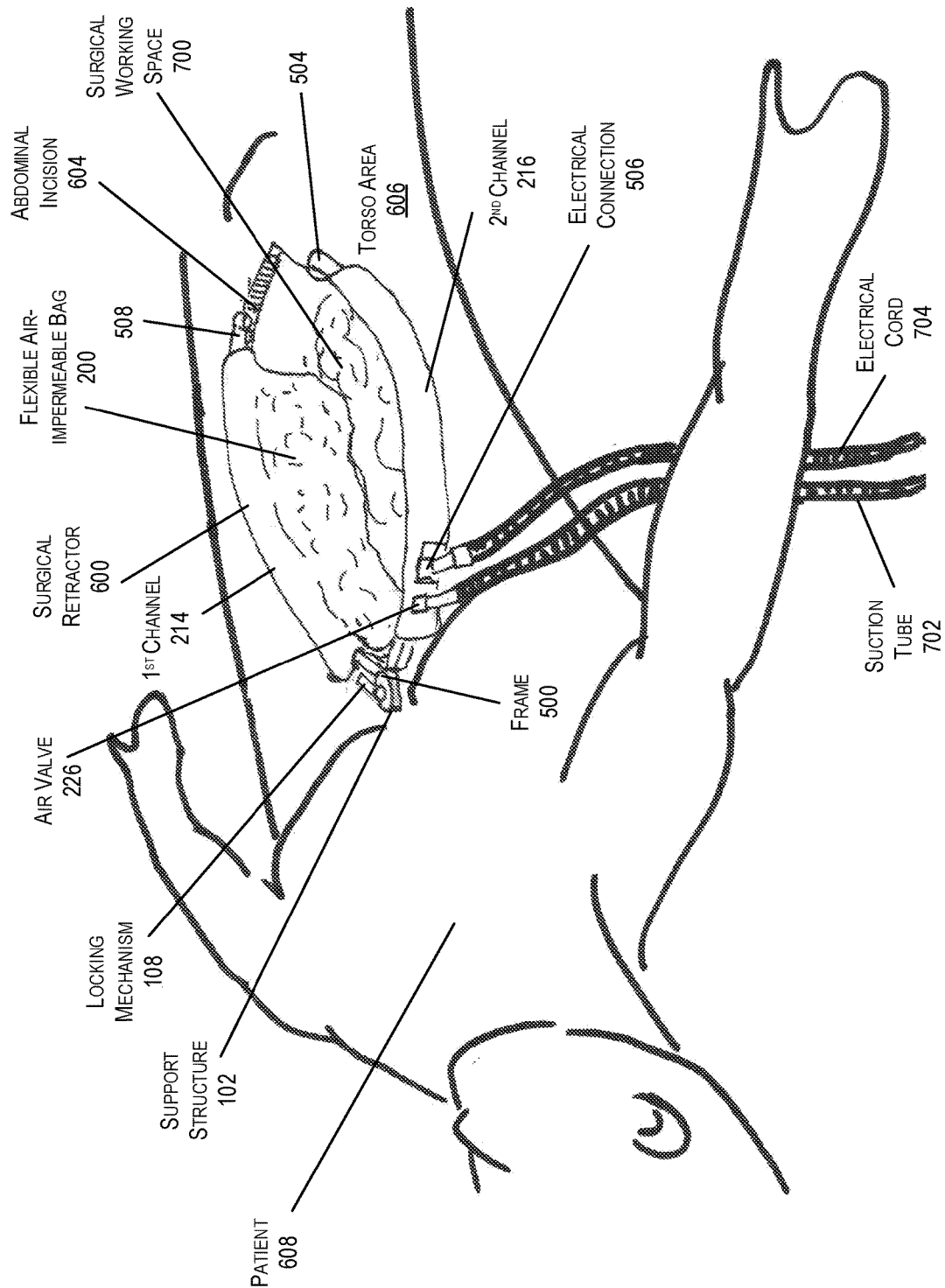
FIG. 7 is perspective view of an example of an implementation of the frame having a lighting system in accordance with the present disclosure.

In FIG. 7, an example frame 700 having a lighting system 702 is shown in accordance with the present disclosure. In this example, the second extending arm 704 may include the lighting system 702 that runs along the length of the second extending arm 704. As an example, the second extending arm 704 may also include an electrical connection 706 at the end of the second extending arm 704 close to the structural support 102, where the electrical connection 706 is configured to connect to an external power source (not shown) to power the lighting system 702. The lighting system 702 is configured to provide light to the surgical working space in the patient.

It is appreciated by those of ordinary skill in the art that while the lighting system 702 is shown in second extending arm 704, that lighting system 702 may alternatively be located in the first extending arm 708. Alternatively, the lighting system 702 may run along both the first extending arm 708 and the second extending arm 704. In all of these examples, the electrical connection 706 may optionally be located in either the on the first extending arm 708 or the second extending arm 704. The flexible air-impermeable bags disclosed herein may include an opening for receiving electrical connection 706. As a further alternative, the frame 700 may have a battery compartment (not shown) in the support structure 102, first extending arm 708, or second extending arm 704 that includes a battery (not shown) capable of powering the lighting system 702.

In these examples, the first extending arm 708 and the second extending arm 704 may include hollow portions or indentations that are configured to integrate the lighting system 702 into the first extending arm 508 and/or the second extending arm 704. Alternatively, the lighting system 702 may be located on the surfaces of the first extending arm 708 and/or the second extending arm 704. Then again, the lighting system 702 may only include a lighting portion at the end of the first extending arm 708 and/or the second extending arm 704 that extends past the first end 204 and/or the second end 208, respectively.

In embodiments including lighting system 702, the flexible air-impermeable bags disclosed herein may include one or more openings along the length of the first channel and/or the second channel to allow the light produced by the lighting system 702 to illuminate the surgical working space of the patient. Alternatively, the flexible air-impermeable bag 200 may be constructed of transparent material for the first channel 214, the second channel 216, or in its entirety. In some embodiments, the lighting system 702 may include a plurality of light emitting diodes (LEDs). Alternatively, the lighting system 702 may include one or more fiber optic cables providing light to one or more light sources within the lighting system 702.

Figure 8:
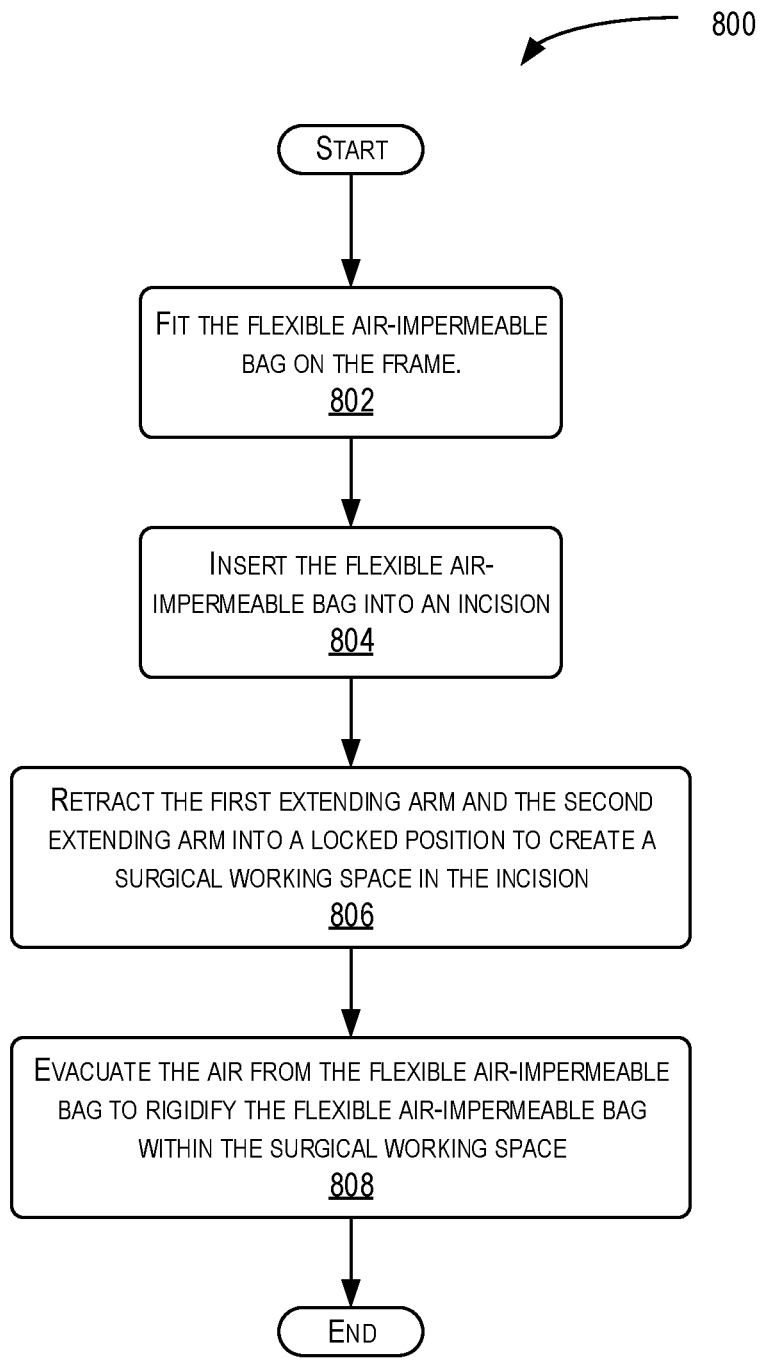
FIG. 8 is a perspective view of example of an implementation of the surgical retractor being inserted into an incision of a torso area of the body of a patient in accordance with the present disclosure.

FIG. 8 is a perspective view of example of an implementation of a surgical retractor 800 being inserted as indicated by arrow 802 into an abdominal incision 804 of a torso area 806 of the body of a patient 808 in accordance with the present disclosure. The resulting positioning of surgical retractor 800 is shown in FIG. 9, which is a perspective view of the surgical retractor 800 positioned within the abdominal incision 804 of the torso area 806 in accordance with the present disclosure. The surgical retractor 800 is shown with its frame in a locked position and with the air in the flexible air-impermeable bag having been evacuated from the interior region 202. In this example, the support structure 102 is adjustable and is configured to move the first extending arm 704 and second extending arm 708 from a relaxed position to the locked position within the abdominal incision 804. The locking mechanism 108 locks the surgical retractor 800 in the locked position and the now rigid flexible air-impermeable bag 200 pushes, positions, and holds the intra-incision contents (such as, for example, tissue and/or organs) within torso area 806 to form a surgical working space 900 within the abdominal incision 804 of the torso area 806. The surgical working space 900 allows a surgeon to have an improved field of view for performing surgery on the patient 608. In this example, a suction tube 902 is shown fluidly connected to the air valve 226. The suction tube 902 is fluidly connected to an external pump (not shown) that suctions the air from within the interior region 202 to compresses the plurality of beads 218 into a tight physical structure that effectively creates a rigid approximately V-shaped or elipse-shaped wall within the abdominal incision 804 that holds the intra-incision contents within torso area 806 away from the surgical working space 900. In this example, an electrical cord 904 is also shown electrically connected to the electrical connection 706 of the surgical retractor 800 to power the lighting system 702 of the frame 700. As discussed earlier, the lighting system 702 is optional and may be powered by either an external energy source (not shown) connected to the electrical cord 904 or via an internal battery within the frame 700. Moreover, while this example shows the electrical connection 706 physically connected to the first extending arm 708, as discussed earlier the electrical connection 706 may alternatively be physically connected to the second extending arm 704. Furthermore, as discussed earlier, the lighting system 702 may include one or more fiber optic cables that are used to provide light energy to one or more light sources within the lighting system 702. In such embodiments, the electrical cord 904 may be a fiber optic cable in optically connected to an external optical light source (not shown). In an example of operation, the lighting system 702 provides for the illumination of the surgical working space 900 to provide an improved field of view for performing surgery on the patient 808.

Turning to FIG. 10, a flowchart of a method 1000 of using the surgical retractors disclosed herein is shown in accordance with the present disclosure. The method starts by fitting 1002 the flexible air-impermeable bag 200 or 600 on the frame 100, 500, or 700, inserting 1004 the flexible air-impermeable bag 200 or 600 into the incision 804, and positioning 1006 the first extending arm 104, 508, or 708 and second extending arm 106, 510, or 704 to the locked position creating the surgical working space 900 within the incision 804. The method 1000 then evacuates 1008 the air from the flexible air-impermeable bag 200 or 600, via the air valve 226, to rigidify the flexible air-impermeable bag 200 or 600 within the surgical working space 900. The method 1000 then ends.

To the extent that terms "includes," "including," "has," "contains," and variants thereof are used herein, such terms are intended to be inclusive in a manner similar to the term "comprises" as an open transition word without precluding any additional or other elements. Moreover, conditional language such as, among others, "can," "could," "might" or "may," unless specifically stated otherwise, are understood within the context to present that certain examples include, while other examples do not include, certain features, elements and/or steps. Thus, such conditional language is not generally intended to imply that certain features, elements and/or steps are in any way required for one or more examples or that one or more examples necessarily include logic for deciding, with or without user input or prompting, whether certain features, elements and/or steps are included or are to be performed in any particular example. Conjunctive language such as the phrase "at least one of X, Y or Z," unless specifically stated otherwise, is to be understood to present that an item, term, etc. may be either X, Y, or Z, or a combination thereof.

All of the methods and processes described above may be embodied in, and fully automated via, software code modules executed by one or more general purpose computers or processors. The code modules may be stored in any type of computer-readable storage medium or other computer storage device. Some or all of the methods may alternatively be embodied in specialized computer hardware.

It is claimed:

1. A surgical retractor for positioning within a surgical working space within a body of a patient, the surgical retractor comprising:
   a frame having
      a support structure,
      a first extending arm and a second extending arm that both extend from the support structure, and a locking mechanism configured to lock the first extending arm and the second extending arm into a locked position;
a flexible air-impermeable bag surrounding an interior region and extending from a first end through a central region to a second end;
a first port in the central region, the flexible air-impermeable bag surrounding a first channel that extends from the first port towards the first end;
a second port in the central region, the flexible air-impermeable bag surrounding a second channel that extends from the second port toward the second end; and
a plurality of beads within the interior region of the flexible air-impermeable bag,
wherein
the first channel is configured to receive the first extending arm,
the second channel is configured to receive the second extending arm, and
the flexible air-impermeable bag is configured to rigidify about the plurality of beads in response to air being evacuated from the interior region to position and hold intra-incision contents within the surgical working space within the body of the patient.

2. The surgical retractor of claim 1, wherein the frame is constructed of metal, plastic, or ceramic.

3. The surgical retractor of claim 1, wherein the first extending arm and the second extending arm are metal, plastic, or ceramic rods.

4. The surgical retractor of claim 1, further including an air valve connected to the flexible air-impermeable bag, wherein the air valve is configured to regulate air flow into and out of the interior region.

5. The surgical retractor of claim 4, wherein the flexible air-impermeable bag is configured to be positioned within a torso portion of the body of the patient.

6. The surgical retractor of claim 4, wherein the support structure is adjustable and is configured to move the first extending arm and second extending arm from a relaxed position to the locked position within the body of the patient.

7. The surgical retractor of claim 6, wherein the flexible air-impermeable bag is configured to rigidify about the plurality of beads from the evacuation of air through the air valve.

8. The surgical retractor of claim 1, further including a lighting system within the frame configured to illuminate the surgical working space.

9. The surgical retractor of claim 8, wherein the lighting system includes a first light source on the first extending arm and a second light source within the second extending arm.

10. The surgical retractor of claim 9, wherein the lighting system includes one or more fiber optic cables.

11. The surgical retractor of claim 8, wherein the lighting system includes a light emitting diode.

12. A surgical retractor, comprising:
a flexible air-impermeable bag surrounding an interior region and extending from a first end through a central region to a second end;
a first port in the central region, the flexible air-impermeable bag surrounding a first channel that extends from the first port towards the first end;
a second port in the central region, the flexible air-impermeable bag surrounding a second channel that extends from the second port toward the second end; and
a plurality of beads within the interior region of the flexible air-impermeable bag,
wherein the flexible air-impermeable bag is configured to rigidify about the plurality of beads in response to air being evacuated from the interior region to position intra-incision contents within a surgical working space in a patient.

13. The surgical retractor of claim 12, further including a frame having a first extending arm and a second extending arm, wherein the first extending arm extends through the first port and the first channel to the first end and the second extending arm extends through the second port and the second channel to the second end.

14. The surgical retractor of claim 13, wherein the frame is constructed of metal, plastic, or ceramic.

15. The surgical retractor of claim 13, wherein the frame further includes a support structure.

16. The surgical retractor of claim 12, further including an air valve connected to the flexible air-impermeable bag, wherein the air valve is configured to regulate air flow into and out of the interior region.

17. The surgical retractor of claim 16, wherein the flexible air-impermeable bag is configured to be positioned within a torso portion of a patient.

18. The surgical retractor of claim 12, wherein the flexible air-impermeable bag is rigid from the evacuation of air from the interior region.

19. A method for positioning a surgical retractor within an incision of a body of a patient, the method comprising:
fitting a flexible air-impermeable bag on a frame having a first extending arm and a second extending arm, wherein the flexible air-impermeable bag has an interior region and a first channel and a second channel extending through the flexible air-impermeable bag that are isolated from the interior region and includes a plurality of beads within the interior region of the flexible air-impermeable bag, the first channel receiving the first extending arm and the second channel receiving the second extending arm, and
inserting the flexible air-impermeable bag into the incision;
evacuating air from the flexible air-impermeable bag to rigidify the flexible air-impermeable bag about the plurality of beads.

20. The method of claim 19, further including lighting a surgical working space with a lighting system within the frame.

* * * * *